(12) United States Patent
Kreidl et al.

(10) Patent No.: US 6,657,062 B1
(45) Date of Patent: Dec. 2, 2003

(54) N-BENZYLPIPERIDINE AND TETRAHYDROPYRIDINE DERIVATIVES

(75) Inventors: Janos Kreidl, Budapest (HU); Laszlo Czibula, Budapest (HU); Andras Nemes, Budapest (HU); Ida Deutschne Juhasz, Budapest (HU); Eva Werkne Papp, Budapest (HU); Juidit Nagyne Bagdy, Budapest (HU); Laszlo Dobay, Budapest (HU); Istvan Hegedus, Budapest (HU); Kalman Harsanyi, Budapest (HU); Istvan Borza, Budapest (HU)

(73) Assignee: Richter Gedeon Vegyesseti Gyar Rt., Budapest (HU)

( * ) Notice: Subject to any disclaimer, the term of this patent is extended or adjusted under 35 U.S.C. 154(b) by 0 days.

(21) Appl. No.: 09/214,099

(22) PCT Filed: Jul. 7, 1997

(86) PCT No.: PCT/HU97/00037

§ 371 (c)(1),
(2), (4) Date: Dec. 28, 1998

(87) PCT Pub. No.: WO98/01424

PCT Pub. Date: Jan. 15, 1998

(30) Foreign Application Priority Data

Jul. 8, 1996 (HU) .......................... P 9601857

(51) Int. Cl.⁷ .................... C07D 211/18; C07D 211/22; C07D 211/30; C07D 211/70
(52) U.S. Cl. ................... 546/197; 546/198; 546/205; 546/206; 546/236; 514/317; 514/319; 514/321
(58) Field of Search ................... 514/317, 319, 514/321; 546/197, 198, 205, 206, 236

(56) References Cited

U.S. PATENT DOCUMENTS

| | | | | |
|---|---|---|---|---|
| 3,982,001 A | * | 9/1976 | Heffe et al. | 546/197 |
| 4,007,196 A | * | 2/1977 | Christensen et al. | 546/197 |
| 4,499,087 A | * | 2/1985 | Treiber et al. | 514/211 |
| 4,585,777 A | * | 4/1986 | Lassen et al. | 514/317 |
| 4,721,723 A | * | 1/1988 | Barnes et al. | 514/321 |
| 5,258,517 A | * | 11/1993 | Zwpp et al. | 546/240 |
| 5,874,447 A | * | 2/1999 | Benneker | 514/321 |
| 6,051,712 A | * | 4/2000 | Binggeli et al. | 546/194 |

FOREIGN PATENT DOCUMENTS

| | | |
|---|---|---|
| EP | 190 496 | 8/1986 |
| EP | 374674 | * 6/1990 |
| WO | WO 96/36636 | * 11/1996 |
| WO | 97/09311 | 3/1997 |

OTHER PUBLICATIONS

Buxton et al. "Solid–state forms of paroxetine hydrochloride" CA 108:192668 (1988).*
Synthesis of Enantiopure . . . , Amai et al., Tetrahedron, vol. 7, No. 6, pp 1591–1594, 1996.
Jr. of Labelled Compounds . . . , Vol XXXIII, No. 8, p 783–794 Wilcocks et al., (1993).

* cited by examiner

*Primary Examiner*—Celia Chang
(74) *Attorney, Agent, or Firm*—Keil & Weinkauf

(57) ABSTRACT

A process is disclosed for the preparation of compounds of the formula (I),

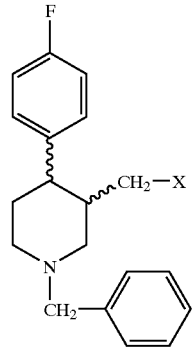

(I)

which compounds are useful as intermediates for the preparation of paroxetine of formula(V).

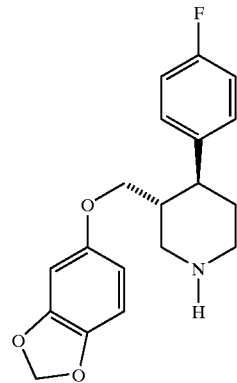

(V)

4 Claims, No Drawings

N-BENZYLPIPERIDINE AND TETRAHYDROPYRIDINE DERIVATIVES

This application is a 371 of PCT/HU97/00037 filed Jul. 7, 1997.

The invention relates to novel N-benzylpiperidine and -tetrahydropyridine derivatives of formula (I),

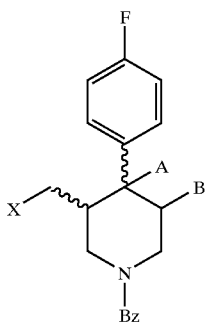

(I)

wherein

X stands for hydroxyl group, halogen or R—SO$_3$-group, wherein R means an optionally substituted alkyl or aryl group;

each of A and B represents hydrogen or, when taken together, they can form a valence bond, as well as to cis and trans isomers, optically active enantiomers and racemates thereof and the salts of these compounds.

The novel compounds of the invention are valuable intermediates for paroxetine [chemically (−)-trans-4-(4-fluorophenyl)-3-(3,4-methylenedioxyphenoxymethyl)piperidine hydrochloride hemihydrate], a drug having antidepressive effect.

Furthermore, the invention relates also to a process for the preparation of the novel compounds of formula (I), wherein X, R, A and B are as defined above, as well as cis and trans isomers, optically active enantiomers and racemates thereof and the salts of these compounds; as well as to the use of these substances for the preparation of paroxetine of formula (V).

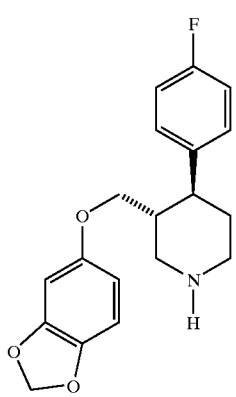

(V)

The process according to the invention comprises reacting a tetrahydropyridine derivative of formula (II)

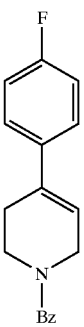

(II)

with formaldehyde in an acidic medium to obtain a novel racemic compound of formula (I), wherein X stands for hydroxyl group, and A together with B means a valence bond.

If desired, after transformation to an acid addition salt and/or resolution, the thus prepared compound is reduced and following the reduction, if desired, after transformation to an acid addition salt and/or after resolution, the obtained cis or trans, racemic or optically active novel compound of formula (I)—wherein X stands for hydroxyl group, and each of A and B represents hydrogen—is reacted with a compound of formula (III)

R—SO$_2$—Y  (III)

or formula (IV)

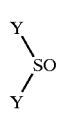

(IV)

wherein R is as defined above and Y stands for halogen; the thus formed novel cis of trans, racemic or optically active compound of formula (I)—wherein X means halogen or R—SO$_3$-group, wherein R is as defined above, and each of A and B stands for hydrogen—is transformed, if desired, to an acid addition salt and/or resolved.

The compound of formula (II) used as starting substance according to our invention, is known and can be prepared similarly to those described in: J. Org. Chem. 12, 894 (1947); or in the Dutch is patent specification No. 6 551 0107.

In the process according to the invention, the starting substance of formula (II) is prepared from N-benzylpiperidone and 4-fluorophenyl magnesium bromide, which are easily available on industrial (large) scales, too.

4-(4-Fluorophenyl)-N-benzyl-1,2,5,6-tetrahydropyridine of formula (II) is transformed with formaldehyde in acidic medium via the Prins reaction to result in a racemic compound of formula (I), wherein X stands for hydroxyl group, and A and B together mean a valence bond. This compound is new, unknown in the literature.

The reaction is preferably carried out by reacting the starting substance with formaldehyde in 45 to 65% aqueous sulfuric acid containing also 1 to 5 molar equivalents of hydrochloric acid at a temperature between 70° C. and 90° C. for 1–2 hours and then isolating the product in the form of its tosylate salt. The new compound of formula (I), wherein X, A and B are as defined above, is an N-benzyltetrahydropyridine derivative, the tosylate salt of which can be isolated with a good efficiency, in a very pure state, in a well-filtrable crystal form.

If desired, the above racemic compound of formula (I)—wherein X means hydroxyl group, and A and B together mean a valence bond—is resolved by using an optically active acid, preferably dibenzoyltartaric acid. The subsequent reaction steps can be continued either with racemic or optically active compounds of formula (I).

In the next step of the process according to our invention, the racemate or optically active form of the novel N-benzyltetrahydropyridine derivative—wherein X stands for hydroxyl group, A and B together mean a valence bond—is reduced to the corresponding novel, racemic cis or trans, or optically active cis or trans N-benzylpiperidine derivative of formula (I), wherein X means hydroxyl group, and each of A and B stands for hydrogen. Trans stereoisomers are formed by reaction of lithium aluminium hydride, but cis stereoisomers are obtained by catalitic hydrogenation. Optically active starting substances give optically active products, whereas racemic products are obtained from racemic starting substances. If desired, a racemic cis product is resolved by employing an optically active acid, advantagenously dibenzoyltartaric acid.

When carrying out the reduction by lithium aluminium hydride, an aprotic solvent, e.g. tetrahydrofuran is used together with 2 to 5 molar equivalents of the reducing agent. The racemic or optically active, respectively trans compounds of formula (I)—wherein X means hydroxyl group, and each of A and B represents hydrogen—are new, unknown in the literature, which are isolated from the reaction mixture as bases or in the form of a salt after decomposition of the reducing agent.

When the reduction is performed by catalytic hydrogenation, either the base or salt form of the starting substance is treated with hydrogen in water or in a nonaqueous medium or in a mixture of solvents, in the presence of (a) catalyst(s) commonly used for the saturation of carbon-carbon double bonds. The saturation of the double bond is nearly selective by using e.g. palladium-on-carbon at room temperature under atmospheric pressure. However, a partial debenzylation also occurs by employing a higher temperature, pressure and greater amount of a catalyst. When a debenzylation occurs, a quantitative re-benzylation can be carried out by a simple reaction. The obtained racemic or optically active, respectively cis compounds of formula (I)—wherein X means hydroxyl group, and each of A and B stands for hydrogen—are obtained from the reaction mixture in the form of a base or salt, preferably as dibenzoyltartarate after removing the catalyst by filtration. An optically active starting compound leads to an optically active product whereas a racemic product is obtained from a racemic starting substance, which is resolved e.g. by using dibenzoyltartaric acid to result in the aimed (+)-cis enantiomer. The cis racemic or optically active compounds, respectively of formula (I)—wherein X, A and B are as defined above—are similarly unknown in the literature.

The racemic cis or trans and optically active cis or trans compounds of formula (I)—wherein X means hydroxyl group, and each of A and B stands for hydrogen—are made even more useful for participating at subsequent (other) condensation reactions by transforming the above hydroxymethyl compounds to racemic cis or trans or optically active, respectively cis or trans compounds of formula (I)—wherein X stands for halogen or R—SO$_3$- group, wherein R means an optionally substitued alkyl or aryl group, and each of A and B represents hydrogen. These latter compounds of formula (I) contain an easily cleavable leaving group and therefore, they are particularly useful to prepare phenol ether type compounds. It was found that compounds of this type can be transformed in an inert (indifferent) solvent (such as a chlorohydrocarbon) at room temperature, in the presence or absence of an acid binding agent, very rapidly and quantitatively with compounds of formula (III)—wherein Y means a halogen, R is as defined above, e.g. $C_{1-4}$alkil, phenyl or tolyl group—such as methanesulfonyl chloride, benzenesulfonyl chloride, p-toluenesulfonyl chloride or with a compound of formula (IV), wherein Y is as defined above, to give compounds of formula (I), wherein X, R, Y, A and B are as defined above. These compounds are similarly unknown in the literature.

The configuration of compound of formula (I)—wherein X means hydroxyl group, and each of A and B stands for hydrogen—is not changed in their reaction with the reagents (reactants) of formula (III) or (IV): i.e. cis compounds are obtained from cis substances, whereas trans substances lead to trans compounds.

After or without isolation, these novel compounds, prepared by using the process according to the invention, can very advantagenously be employed (utilized) for the preparation of racemic or optically active trans-1-benzyl-4-(4-fluorophenyl)-3-(3,4-methylenedioxyphenoxymet-hyl) piperidine [abbreviated: N-benzylparoxetine] compounds. Paroxetine can be synthetized by catalytic debenzylation of N-benzylparoxetine or its acid addition salt; after resolution of the obtained compound or its salt, the base is liberated from the optically active salt formed, or the base is directly converted to hydrochloride hemihydrate.

The above methods are very useful to prepare paroxetine on large/industrial scales in a simple way.

The following Examples are given to illustrate the novel compounds according to the invention and the process for their preparation as well as the preparation of paroxetine base and its salts.

EXAMPLE 1

Preparation of 1-Benzyl-4-(4-fluorophenyl)-1,2,5,6-tetrahydro-pyridine Tosilate

After weighing 80 g (0.28 mol) of 1-benzyl-4-(4-fluorophenyl)-4-hydroxypiperidine and 69.0 g (0.364 mol) of p-toluenesulfonic acid monohydrate to 400 ml of chlorobenzene under stirring, the reaction mixture is boiled under reflux for 3 hours while distilling out water introduced as crystal water and the water formed in the reaction. After termination of the reaction, 100 ml of chlorobenzene are additionally distilled out under atmospheric pressure. After cooling the mixture obtained to 0° C., the precipitated title product is filtered, twice washed with 10 ml of cold acetone each and dried on the air to give a yield of 90.5 g (73%), m.p.: 180–182° C.

EXAMPLE 2

Preparation of (±)-1-Benzyl-4-(4-fluorophenyl)-3-hydroxy-methyl-1,2,3,6-tetrahydropyridine Tosylate After adding portionwise 140 ml of concentrated sulfuric acid to 160 ml of water under stirring and cooling, 40 ml of concentrated hydrochloric acid, 88 g (0,2 mol) of 1-benzyl-4-(4-fluorophenyl)-1,2,5,6-tetrahyropyridine tosylate and 8 g (0.267 mol) of paraformaldehyde are added at room temperature. The mixture is stirred at 80° C. for one hour, 300 ml of toluene and then 300 ml of water are added. Finally, the mixture is alkalinized by adding a solution of 240 g of sodium hydroxide in 500 ml of water at a temperature not higher than 40° C. under cooling. After separating the mixture at 30° C., the aqueous layer is extracted with 50 ml of toluene. The combined toluene solution is extracted successively with 3.2 ml of concentrated hydrochloric acid diluted with 200 ml of water, and then with the solution of 1 ml of concentrated hydrochloric acid in 100 ml of water. After drying, the organic phase over anhydrous magnesium sulfate and filtering, the filtrate is evaporated to dryness under reduced pressure. The evaporation residue is a light yellow thick oil, which is dissolved in 100 ml of acetone and 30 g of p-toluenesulfonic acid monohydrate are added. The crystalline precipitate is stirred at 10° C. for one hour, then filtered, twice washed with 10 ml of acetone each, and dried to yield 56 g (59.7%) of the title compound, m.p.: 170–172° C.

EXAMPLE 3

Preparation of (−)-1-Benzyl-4-(4-fluorophenyl)3-hydroxymethyl-1,2,3,6-tetrahydropyridine To a solution of 44.7 g (0.15 mol) of (±)-1-benzyl-4-(4-fluorophenyl)-3-hydroxymethyl-1,2,3,6-tetrahydropyridine in 70 ml of acetone, 56,4 g of (−)-L-dibenzoyltartaric acid monohydrate dissolved in 180 ml of acetone are added at room temperature, then the mixture is stirred at room temperature for 5 hours. The precipitated (−)-L-dibenzoyltartarate of the title compound is filtered at 10° C., twice washed with 20 ml of cold acetone each and dried on air to give 42 g (85.6%) of product, m.p.: 126–128° C.; $[\alpha]_D^{20}$−93.5° (c=2, methanol).

After suspending the thus obtained salt in 200 ml of water, 200 ml of methylene chloride (dichloromethane) are added and the mixture is alkalinized under stirring by adding the solution of 4.5 g of sodium hydroxide in 20 ml of water. After separation of the phases, the aqueous layer is extracted with 50 ml of dichloromethane. The combined organic phase is dried over anhydrous magnesium sulfate and after filtration, the filtrate is evaporated to solvent-free under reduced pressure to yield 18.5 g (97%) of title compound, m.p.: 67–68.5° C. (after recrystallization from diisopropyl ether), $[\alpha]_D^{20}$−73.1° (c=1, chloroform).

EXAMPLE 4

Preparation of (+)-1-Benzyl-4-(4-fluorophenyl)3-hydroxymethyl-1,2,3,6-tetrahydropyridine A solution containing 5.64 g of (+)-D-dibenzoyltartaric acid monohydrate in 20 ml of acetone is added to 4.47 g (0.015 mol) of (±)-1-benzyl-4-(4-fluorophenyl)3-hydroxymethyl-1,2,3,6-tetrahydropyridine at room temperature. Then the mixture is stirred at room temperature for 4 hours.

The precipitated (+)-D-dibenzoyltartarate salt of the title compound is filtered at 10° C., twice washed with 2 ml of cold acetone each and dried on air to yield 4.2 g (83.2%) of product, m.p.: 128–131° C.; $[\alpha]_D^{20}$+93.2° (c=2, methanol).

After suspending the thus obtained salt in 25 ml of water and adding 35 ml of dichloromethane, the mixture is alkalinized by a solution containing 0.6 g of sodium hydroxide in 10 ml of water. After separation of the phases, the aqueous layer is extracted with 10 ml of dichloromethane. The combined organic phase is dried over magnesium sulfate, the drying agent is filtered and the filtrate is evaporated to solvent-free under reduced pressure to result in 1.79 g (97%) of title compound, m.p.: 68–68.5° C.; $[\alpha]_D^{20}$+74.20 (c=1, chloroform).

EXAMPLE 5

Preparation of (±)-Trans-1-Benzyl-4-(4-fluorophenyl)-3-hydroxy-methylpiperidine 5 g (0.13 mol) of lithium aluminium hydride are suspended at 0° C. in 150 ml of absolutized peroxide-free tetrahydrofuran under an inert atmosphere in a dry equipment with exclusion of any moisture. A solution containing 36 g (0.12 mol) of (±)-1-benzyl-4-(4-fluorophenyl)-3-hydroxymethyl-1,2,3,6-tetrahydropyridine in 150 ml of absolutized peroxide-free tetrahydrofuran is dropwise added under cooling and stirring at a temperature not higher than 20° C. Thereafter, the mixture is boiled under reflux for 4 hours. After termination of the reaction 10 ml of water are dropped to the mixture under cooling, at a highest temperature of 20° C. After stirring for one hour 10 g of celite are added, filtered, and the substance remaining on the filter is washed in two portions with a total of 100 ml of tetrahydrofuran. After evaporating the filtrate to solvent-free under reduced pressure, the residue is dissolved in 200 ml of dichloromethane and extracted twice with 50 ml of water each. The organic phase is dried over magnesium sulfate, and after removing the drying agent by filtration, the filtrate is evaporated to solvent-free under reduced pressure. The evaporation residue is recrystallized from 30 ml of cyclohexane to yield 27.8 g (77%) of the title compound, m.p.: 83–84° C. The p-toluenesulfonic acid salt of the product can be recrystallized from acetone, m.p.: 148–150° C.

EXAMPLE 6

Preparation of (−)-Trans-1-Benzyl-4-(4-fluorophenyl)-3-hydroxy-methylpiperidine

To a suspension containing 0.8 g (0.021 mol) of lithium aluminium hydride in 20 ml of absolutized peroxide-free tetrahydrofuran at 0° C. in a dry equipment under inert environment with exclusion of moisture, a solution containing 5 g (0.0168 mol) of (+)-1-benzyl-4-(4-fluorophenyl)-3-hydroxymethyl-1,2,3,6-tetrahydropiridine in 30 ml of absolutized peroxide-free tetrahydrofuran is portionwise added under cooling and stirring at a highest temperature of 20° C. Then, the mixture is boiled under reflux for 4 hours. After termination of the reaction 1.5 ml of water are added to the mixture, and after stirring for one hour and adding 2 g of celite it is filtered and the substance remaining on the filter is twice washed with 15 ml of tetrahydrofuran each. After evaporating the filtrate to solvent-free under reduced pressure, the residue is dissolved in 50 ml of dichloromethane and extracted twice with 10 ml of water each. The organic phase is dried over magnesium sulfate and after removing the drying agent by filtration, the filtrate is evaporated to solvent-free under reduced pressure.

The evaporation residue represents the title product with a weight of 5 g (94.5%) which becomes crystalline by itself After recrystallization from isopropyl alcohol, the hydrochloride of the compound melts at 63–65° C.; $[\alpha]_D^{20}$−10.3° (c=1, methanol).

EXAMPLE 7

Preparation of (±)-cis-1-Benzyl-4-(4-fluorophenyl)-3-hydroxy-methylpiperidine

To a suspension containing 46.85 g (0.1 mol) of (+)-1-benzyl-4-(4-fluorophenyl)-3-hydroxy-methyl-1,2,3,6-tetrahydropyridine tosylate in 200 ml of dichloromethane, a solution of 4.4 g (0.11 mol) of sodium hydroxide in 100 ml of water is added and the mixture is stirred until homogeneous phases are achieved. After separating the organic phase from the aqueous layer, and extracting the aqueous layer with 50 ml of dichloromethane, the combined organic solution is dried on a drying agent and the filtrate is evaporated to solvent-free, the evaporation residue is dissolved in 120 ml of ethanol and hydrogenated in the presence of 1.5 g of 10% palladium-on-carbon catalyst at 30° C. under atmospheric pressure. After saturation, the catalyst used is filtered and the filtrate is evaporated to solvent-free. The residue is treated with diisipropyl ether and filtered to yield 20.0 g (67.0%) of the title compound, m.p.: 89–91° C.

EXAMPLE 8

Preparation of (±)-cis-1-Benzyl-4-(4-fluorophenyl)-3-hydroxy-methylpiperidine

A solution containing 4.4 g (0.11 mol) of sodium hydroxide in 100 ml of water is added to the suspension of 46.85 g (0.1 mol) of (±)-1-benzyl-4-(4-fluorophenyl)-3-hydroxy-methyl-1,2,3,6-tetrahydro-pyridine tosylate in 200 ml of dichloromethane and the mixture is stirred until homogeneous phases are formed. After separating the organic phase from the aqueous layer and extracting the aqueous layer with 50 ml of dichloromethane, the combined organic phase is dried over a drying agent and the filtrate is evaporated to solvent-free. The evaporation residue is dissolved in a mixture containing 120 ml of water, 12 ml of glacial acetic acid and 6 ml of concentrated hydrochloric acid and hydrogenated at 45° C. in a pressure-tight autoclave in the presence of 1.5 g of 10% palladium-on-carbon catalyst. After saturation the catalyst used is filtered out at room temperature. After adding 80 ml of dichloromethane to the filtrate the pH value is adjusted to 9 by adding 40% sodium hydroxide solution. The organic phase is separated, the aqueous layer is extracted with 20 ml of dichloromethane. After drying the combined organic solution over a drying agent, and evaporating the filtrate to solvent-free, the evaporation residue is treated with diisopropyl ether and filtered to give 21.8 g (73%) of title product, m.p.: 89–91° C.

EXAMPLE 9

Preparation of (+)-cis-1-Benzyl-4-(4-fluorophenyl)-3-hydroxy-methylpiperidine

After suspending 65.5 g (0.1 mol) of (−)-1-benzyl-4-(4-fluorophenyl)-3-hydroxymethyl-1,2,3,6-tetrahydropyridine L-diben-zoyltartarate in the mixture of 200 ml of dichloromethane and 100 ml of water, 30 ml of concentrated aqueous ammonia solution are added under stirring to achieve homogeneous phases at a pH value of 9. The phases are separated, the aqueous layer is extracted with 50 ml of dichloromethane, then the combined organic phase is dried over a drying agent and the filtrate is evaporated to solvent-free. The evaporation residue is dissolved in a mixture containing 120 ml of water, 12 ml of glacial acetic acid and 6 ml of concentrated hydrochloric acid and hydrogenated at 45° C. in the presence of 1.5 g of 10% palladium-on-carbon catalyst. After saturation the catalyst used is filtered at room temperature. After adding 80 ml of dichloromethane to the filtrate and alkalinizing to pH 9 by adding 40% sodium hydroxide solution, the organic phase is separated and the aqueous layer is extracted with 20 ml of dichloromethane. The combined organic phase is dried over a drying agent, filtered and the filtrate is evaporated to solvent-free. The evaporation residue is dissolved in 100 ml of acetone and a solution containing 36.9 g (0.098 mol) of (−)-L-dibenzoyltartaric acid monohydrate in 150 ml of acetone is added. The precipitated crystals are filtered at 5° C.

The product filtered out represents the (−)-L-dibenzoyltartarate of the title compound with a weight of 51.2 g (78%), m.p.: 118–119° C.; $[\alpha]_D^{20}$ −29.5° (c=1, methanol).

The title compound is prepared by liberating the base from the obtained salt. After suspending the salt in the mixture of 100 ml of water and 100 ml of dichloromethane, the pH value of the mixture is adjusted to 9 by adding concentrated aqueous ammonia solution under stirring. After separation, the aqueous layer is extracted with 30 ml of dichloromethane. After drying the combined organic phase over a drying agent and filtration, the filtrate is evaporated to solvent-free to yield 22.6 g of title compound (the efficiency of liberation of the base is 97%), mp.p.: 65–66° C.; $[\alpha]_D^{20}$ +54.1° (c=1, chloroform).

EXAMPLE 10

Preparation of (−)-cis-1-Benzyl-4-(4-fluorophenyl)-3-hydroxy-methylpiperidine L-dibenzoyltartarate A solution containing 37.6 g (0.1 mol) of (−)-L-dibenzoyltartaric acid monohydrate in 150 ml of acetone is added to a solution containing 29.8 g (0.1 mol) of (±)-cis-1-benzyl4-(4-fluorophenyl)-3-hydroxymethylpiperidine in 100 ml of acetone at room temperature. The mixture is stirred for 6 hours, then the crystalline title product is filtered at 5° C. to result in a yield of 29.55 g (90%), m.p.: 118–119° C.; $[\alpha]_D^{20}$ −9.6° (c=1, methanol).

EXAMPLE 11

Preparation of (±)-cis-1-Benzyl-4-(4-fluorophenyl)-3-mesyloxy-methylpiperidine

To a solution containing 14.9 g (0.05 mol) of (±)-cis-1-benzyl-4-(4-fluorophenyl)-3-hydroxymethylpiperidine in 75 ml of dichloromethane, 5.8 g (0.0574 mol) of triethylamine are added at room temperature, then 6.6 g (0.0576 mol) of methanesulfonyl chloride are added during 10 to 15 minutes. The mixture is stirred at the above temperature for 3 hours, after termination of the reaction 40 ml of water are added to the mixture and the pH value is adjusted to 8 by the means of 10% sodium hydrogen carbonate solution. After separating the phases, the aqueous layer is extracted with 20 ml of dichloromethane. After washing the combined organic phase with 20 ml of water and drying over a drying agent, the mixture is filtered and the filtrate is evaporated to solvent-free to yield 18.3 g (97%) of title compound, m.p.: 49–51° C.

EXAMPLE 12

Preparation of (+)-cis-1-Benzyl-4-(4-fluorophenyl)-3-mesyloxy-methylpiperidine

The process described in Example 11 is followed, except that 14.9 g (0.05 mol) of (+)-cis-1-benzyl-4-(4-fluorophenyl)-3-hydroxy-methylpiperidine are weighed in instead of 14.9 g (0.05 mol) of (±)-cis-1-benzyl-4-(4-fluorophenyl)-3-hidroxy-methylpiperidine.

The title compound is obtained in a yield of 18.3 g (97%) in the form of a light yellow thick oil; $[\alpha]_D^{20}$+70.8° (c=1, chloroform). The hydrochloride prepared therefrom in acetone melts at 128–130.5° C.; $[\alpha]_D^{20}$+46° (c=1, methanol).

EXAMPLE 13

Preparation of (±)-trans-1-Benzyl-4-(4-fluorophenyl)-3-mesyl-oxymethylpiperidine The process described in Example 11 is followed, except that 14.9 g (0.5 mol) of (+)-trans-1-benzyl-4-(4- fluorophenyl)-3-hydroxy-methylpiperidine are weighed in instead of 14.9 g (0.05 mol) of (±)-cis-1-benzyl-4-(4-fluorophenyl)-3-hydroxymethylpiperidine.

The title compound is obtained in a yield of 18.3 g (97%), in the form of a light yellow thick oil. The fumarate salt prepared therefrom in acetone melts at 161–163° C.

EXAMPLE 14

Preparation of (−)-trans-1-Benzyl-4-(4-fluorophenyl)-3-mesyloxy-methylpiperidine The process described in Example 11 is followed, except that 14.9 g (0.05 mol) of (−)-trans-1-benzyl-4-(4-fluorophenyl)-3-hydroxy-methylpiperidine are weighed in instead of 14.9 g (0.05 mol) of (±)-cis-1-benzyl-4-(4-fluorophenyl)-3-hydroxymethylpiperidine The title compound is obtained in a yield of 18.1 g (96%) in the form of a light yellow thick oil; The fumarate salt prepared therefrom in acetone melts at 153–155° C., $[\alpha]_D^{20}$−7.9° (c=1, methanol).

EXAMPLE 15

Preparation of (+)-cis-1-Benzyl-4-(4-fluorophenyl)-3-(benzene-sulfonyloxymetil)piperidine To a solution containing 3.73 g (0.0125 mol) of (+)-cis-1-benzyl-4-(4-fluorophenyl)-3-hydroxymethylpiperidine in 20 ml of dichloromethane, 1.45 g (0.0144 mol) of triethylamine, then 2.5 g (0.0144 mol) of benzenesulfonyl chloride are added at room temperature, and subsequently, it is stirred at the same temperature for 5 hours. After completion of the reaction, 10 ml of water are added to the mixture and it is alkalinized to pH 8 by adding 10% sodium hydrogen carbonate solution. After separation of the phases, the aqueous layer is extracted with 10 ml of dichloromethane. The combined organic phase is washed with 10 ml of water, dried over a drying agent and filtered. The filtrate is evaporated to solvent-free and the residue is recrystallized from methanol.

The crystalline precipitate is filtered at 0° C., washed with cold methanol and dried on air to obtain 4.95 g (90%) of title compound, m.p.: 93–95° C.; $[\alpha]_D^{20}$+85.1° (c=1, chloroform).

EXAMPLE 16

Preparation of (+)-cis-1-Benzyl-4-(4-fluorophenyl)-3-(tosyloxy-methylpiperidine

The process described in Example 15 is followed, except that 2.75 g (0.0144 mol) of p-toluenesulfonyl chloride are used instead of 2.5 g (0.0144 mol) of benzenesulfonyl chloride. The title product is obtained in a yield of 5.2 g (92%), m.p.: 74–76° C.; $[\alpha]_D^{20}$+95.9° (c=1, chloroform).

EXAMPLE 17

Preparation of (+)-cis-1-Benzyl-4-(4-fluorophenyl)-3-(chloro-methylpiperidine

To a solution containing 3.73 g (0.0125 mol) of (+)-cis-1-benzyl-4-(4-fluorophenyl)-3-hydroxymethylpiperidine in 20 ml of dichloroethane, 0.5 ml of dimethylformamide and then, at 50 to 55° C. 2.3 g (0.019 mol) of thionyl chloride are added. The mixture is boiled under reflux for 3 hours and subsequently, 10 ml of water are added at room temperature and the mixture is alkalinized to pH 9 by adding 10% sodium carbonate solution. After separation the aqueous layer is extracted with 10 ml of dichloroethane, the combined organic solution is washed with 10 ml of water and dried over a drying agent. After filtration the filtrate is evaporated to solvent-free under reduced pressure.

The evaporation residue represents the title compound, which becomes crystalline by itself. The yield is 3.76 g (94%), m.p.: 56–59° C.; $[\alpha]_D^{20}$+83.6° (c=1, chloroform).

EXAMPLE 18

Use of (−)-trans-1-benzyl-4-(4-fluorophenyl)-3-mesyloxymethylpiperidine for the preparation of paroxetine hydrochloride hemihydrate (paroxetine.HCl.1/2H$_2$O)

a.) Preparation of (−)-trans-1-benzyl-4-(4-fluorophenyl)-3-(3,4-methylenedioxy-phenoxymethyl)piperidine hydrochloride After suspending 7.5 g (0.02 mol) of (−)-trans-1-benzyl4-(4-fluorophenyl)-3-mesyloxymethylpiperidine in the mixture of 20 ml of toluene and 20 ml of isopropanol, 4.13 g (0.03 mol) of sesamol and 3 ml of 50% aqueous sodium hydroxide solution are added. The mixture is boiled under reflux for 15 hours under nitrogen gas and vigorous stirring.

After completion of the reaction and adding 20 ml of toluene and 80 ml of water to the mixture, it is separated at room temperature, the organic layer is extracxted twice with 40 ml of water each and dried over sodium sulfate. After filtering the drying agent, the filtrate is evaporated to solvent-free under reduced pressure. The evaporation residue is dissolved in 25 ml of isopropanol and acidified to pH 2 by adding concentrated hydrochloric acid.

The crystalline precipitate is filtered at 0° C., washed twice with 2 ml of cold acetone each and dried on air to obtain 6.2 g (68%) of title compound, m.p.: 237–239° C., $[\alpha]_D^{20}$−38.1° (c=1, methanol).

b.) Preparation of (−)-trans-4-(4-fluorophenyl)-3-(3,4-methylene-dioxyphenoxymethyl)piperidine (generic name: paroxetine) hydro-chloride hemihydrate A suspension containing 9.1 g (0.02 mol) of (−)-trans-1-benzyl-4-(4-fluorophenyl)-3-(3,4-methylenedioxyphenoxymethyl)piperidine hydrochloride in the mixture of 150 ml of isopropanol and 3 ml of distilled water is hydrogenated in an autoclave in the presence of 0.3 g of 10% palladium-on-carbon catalyst at 30 to 40° C. under $5 \times 10^4$–$10^5$ Pa pressure for 2 to 3 hours. After taking up the hydrogen, the catalyst is filtered at a temperature between 30° C. and 35° C. The volume of the filtrate is reduced to 35 ml by distillation and the solution is crystallized at 0° C. The precipitated product is filtered, twice washed with 2 ml of cold isopropanol each and dried on the air to give 6.55 g (89.5%) of title compound, m.p.: 136–138° C.,$[\alpha]_D^{20}$−86.50° (c=1, methanol).

The water content of the product is 2.44% (measured by Karl Fischer's method).

EXAMPLE 19

Preparation of (±)-trans-1-Benzyl-4-(4-fluorophenyl)-3-(3,4-methylenedioxyphenoxymethyl)piperidine Hydrochloride (VI.HCl)

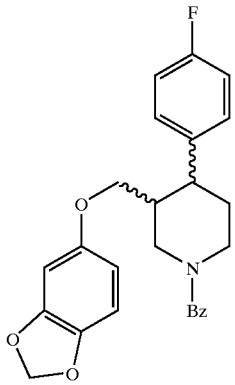

(VI)

To a suspension of 7,54 g (0.02 mol) of (±)-trans-1-benzyl-4-(4-fluorophenyl)-3-mesyloxymethylpiperidine (see Example 13) in the mixture of 20 ml of toluene and 20 ml of isopropanol, 4.13 g (0.03 mol) of sesamol and 3 ml of 50% aqueous sodium hydroxide solution are added. The mixture is boiled under reflux in a nitrogen atmosphere under vigorous stirring for 15 hours.

After taking place of the reaction, the mixture is diluted with 20 ml of toluene and 80 ml of water and separated at room temperature. The organic layer is twice extracted with 40 ml of water each and dried over sodium sulfate. After filtering out the drying agent, the filtrate is evaporated to solvent-free under reduced pressure. The evaporation residue is dissolved in 25 ml of isopropanol and acidified to pH 2 by concentrated hydrochloric acid.

The precipitated crystalline product is filtered at 0° C., twice washed with 2 ml of cold acetone each and dried on air to obtain 6.2 g (68%) of title compound, m.p.: 249–251° C.

EXAMPLE 20

Preparation of (±)-trans-1-Benzyl-4-(4-fluorophenyl)-3-(3,4-methylenedioxyphenoxymethyl)piperidine Hydrochloride (VI.HCl)

To a solution containing 7.54 g (0.02 mol) of (±)-trans-1-benzyl-4-(4-fluorophenyl)-3-mesyloxymethylpiperidine in 40 ml of toluene, a solution of 2.8 g (0.07 mol) of sodium hydroxide in 4.2 ml of water, 0.3 g of tricaprylmethylammonium chloride and 3.0 g (0.022 mol) of sesamol are added. The mixture is boiled under reflux under nitrogen with vigorous stirring for 5 hours. After taking place of the reaction, the mixture is diluted with 30 ml of water, separated at room temperature and the toluene phase is washed 5 times with 30 ml of water each, dried and filtered. After adding 20 ml of isopropanol to the solution the pH value is adjusted to 2 by concentrated hydrochloric acid.

The precipitated product is filtered at 0° C., washed with acetone and dried on air to yield 6.65 g (73%) of title compound, m.p.: 249–251° C.

EXAMPLE 21

Preparation of (−)-trans-1-Benzyl-4-(4-fluorophenyl)-3-(3,4-methylenedioxyphenoxymethyl)piperidine Hydrochloride (VIa.HCl)

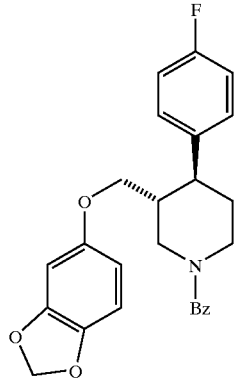

(VIa)

The process described in Example 19 is followed, except that 7.54 g (0.02 mol) of (−)-trans-1-benzyl-4-(4-fluorophenyl)-3-mesyloxymethylpiperidine are weighed in instead of 7.54 g (0.02 mol) of (±)-trans-1-benzyl-4-(4-fluorophenyl)-3-mesyloxymethylpiperidine.

The title compound is obtained in a yield of 6.2 g (68%), m.p. 237–239° C., $[\alpha]_D^{20}$ –38.1° (c=1, methanol).

EXAMPLE 22

Preparation of (−)-trans-4-(4-Fluorophenyl)-3-(3,4-methylene-dioxyphenoxymethyl)piperidine Hydrochloride Hemihydrate (V)

A solution containing 8.4 g (0.02 mol) of (−)-trans-1-benzyl-4-(4-fluorophenyl)-3-(3,4-methylenedioxyphenoxymethyl)piperidine in 120 ml of ethanol is hydrogenated in an autoclave in the presence of 0.6 g of 10% palladium-on-carbon catalyst at 30 to 40° C. under $2 \times 10^5$ Pa pressure for 2 to 3 hours. After taking up the hydrogen, the catalyst is filtered under nitrogen gas and the filtrate is evaporated to solvent-free to give 6.5 g of paroxetine base as evaporation residue in the form of a colourless oil. The product is suspended in 80 ml of water and after adding 2 ml of glacial acetic acid, it is stirred until dissolution. Then, the solution of 2 g of ammonium chloride in 10 ml of water is added to the mixture. After stirring for 4 hours, the precipitated crystalline title product is filtered at 10° C., twice washed with 10 ml of cold water each and dried on air to obtain 6,5 g (89%) of title compound, m.p.: 136–138° C.; $[\alpha]_D^{20}$ –86.6° (c=1, methanol).

The water content of the product is 2.46% (measured by Karl Fischer's method).

EXAMPLE 23

Preparation of (−)-trans-4-(4-Fluorophenyl)-3-(3,4-methylene-dioxyphenoxymethyl)piperidine Hydrochloride Hemihydrate A suspension containing 9.1 g (0.02 mol) of (−)-trans-1-benzyl-4-(4-flurophenyl)-3-(3,4-methylenedioxyphenoxymethyl)piperidine hydrochloride in the mixture of 150 ml of isopropanol and 3 ml of distilled water is hydrogenated in an autoclave in the presence of 0.3 g of 10% palladium-on-carbon catalyst at 30 to 40° C. under $5 \times 10^4 – 10^5$ Pa pressure for 2 to 3 hours. After taking up the hydrogen, the catalyst is filtered at a temperature of 30 to 35° C. The filtrate is concentrated to 35 ml by distillation and the solution is crystallized at 0° C.

The precipitated product is filtered, twice washed with 2 ml of cold isopropanol each and dried on the air to obtain 6.55 g (89.5%) of title copound, m.p.: 136–138° C.; $[\alpha]_D^{20}$ –86.5° (c=1, methanol).

The water content of the product is 2.44% (measured by Karl Fischer's method).

EXAMPLE 24

Preparation of (−)-trans-4-(4-Fluorophenyl)-3-(3,4-methylene-dioxyphenoxymethyl)piperidine Hydrochloride Hemihydrate A suspension containing 9.1 g (0.02 mol) of (±)-trans-1-benzyl-4-(4-fluorophenyl)-3-(3,4-methylenedioxyphenoxymethyl)piperidine hydrochloride in the mixture of 100 ml of chloroform and 50 ml of water is alkalinized to pH 9 by adding concentrated aqueous ammonia solution. After separation of the phases, the aqueous layer is extracted with 20 ml of chloroform. The combined organic phase is dried over magnesium sulfate and, after filtering the drying agent the solution is evaporated to solvent-free. The evaporation residue is dissolved in 120 ml of ethanol and hydrogenated in an autoclave in the presence of 0.8 g of 10% palladium-on-carbon catalyst at 40° C., under $5 \times 10^5$ Pa pressure for 2 to 3 hours. After taking up the hydrogen, the catalyst is filtered and the filtrate is evaporated to solvent-free. The evaporation residue (weighing 6.6 g) is dissolved in 80 ml of methanol, a solution of 3 g (0.02 mol) of (+)-D-tartaric acid in 20 ml of methanol is added at room temperature and the mixture is stirred for 5 hours. The precipitated crystalline product is filtered to yield 3.2 g (66%) of (−)-trans-4-(4-flurophenyl)-3-(3,4-metylenedioxyphenoxymethyl)piperidine (+)-D-tartarate, m.p.: 178–180° C.; $[\alpha]_D^{20}$ –50.5° (c=1, dimethylformamide).

The above salt is stirred at 40° C. with a solution of 1.1 g of ammonium chloride in 25 ml of water for 2 hours, then the crystalline precipitate is filtered at 10° C., washed with cold water and dried on the air to give 2.1 g (85%) of title compound, m.p.: 136–138° C.; . $[\alpha]_D^{20}$ –86,4° (c=1, methanol The water content of the product is 2.45% (measured by Karl Fischers method).

EXAMPLE 25

Preparation of (±)-trans-1-Benzyl-4-(4-fluorophenyl)-3-(3,4-methylenedioxyphenoxymethyl)piperidine Hydrochloride (VI.HCl)

To a solution containing 7.54 g (0.02 mol) of (±)-cis-1-benzyl-4-(4-fluorophenyl)-3-mesyloxymethylpiperidine in 120 ml of xylene 3 g (0.022 mol) of sesamol and 5.5 g (0.04 mol) of finely ground anhydrous potassium carbonate are added and the mixture is boiled under reflux under nitrogen gas while vigorously stirring for 2.5 hours. After taking place of the reaction, 50 ml of water are added to the mixture. After separation, the organic phase is washed with water until neutral, dried over a drying agent, filtered and the filtrate is evaporated to solvent-free under reduced pressure. The evaporation residue is dissolved in 35 ml of isopropanol and acidified to pH 2 by aqueous concentrated hydrochloric acid.

The precipitated product is filtered at 0° C., washed with acetone and dried on air to yield 6.2 g (68%) of title compound, m.p.: 249–251° C.

EXAMPLE 26

Preparation of (−)-trans-1-Benzyl-4-(4-fluorophenyl)-3-(3,4-methylenedioxyphenoxymethyl)piperidine Hydrochloride (VIa.HCl)

To a solution of 7.54 g (0.02 mol) of (+)-cis-1-benzyl-4-(4-fluorophenyl)-3-mesyloxymethylpiperidine in 120 ml of methyl isobutyl ketone 3 g (0.022 mol) of sesamol, 5.5 g (0.04 mol) of anhydrous potassium carbonate are added and the mixture is boiled under reflux under nitrogen gas for 3.5 hours. After taking place of the reaction, 50 ml of water are added to the mixture, after separation the organic phase is washed with water until neutral, dried over a drying agent, filtered and the filtrate is evaporated to solvent-free under reduced pressure. The evaporation residue is dissolved in 35 ml of isopropanol and acidified to pH 2 by aqueous concentrated hydrochloric acid.

The precipitated product is filtered at 0° C., washed with acetone and dried on air to result in 6.3 g (69%) of title compound, m.p.: 236–238° C.; $[\alpha]_D^{20}$ –37.9° (c=1, methanol

EXAMPLE 27

Preparation of (−)-trans-1-Benzyl-4-(4-fluorophenyl)-3-(3,4-methylenedioxyphenoxymethyl)piperidine (VIa.)

To a solution containing 7.54 g (0.02 mol) of (+)-cis-1-benzyl-4-(4-fluorophenyl)-3-mesyloxymethylpiperidine in 120 ml of tertiary butanol, 3 g (0.022 mol) of sesamol and 3.35 g (0.03 mol) of potassium tertiary butoxide are added and the mixture is boiled under reflux for 12 hours. After completion of the reaction the mixture is evaporated and 100 ml of dichloromethane and 50 ml of water are added to the residue. After separation, the organic phase is washed with water until neutral, dried over a drying agent and after filtration the filtrate is evaporated to solvent-free. The evaporation residue is recrystallized from 25 ml of isopropanol. The precipitated product is filtered at 0° C. to obtain 5.37 g (64%) of title compound, m.p.: 98–100° C.; $[\alpha]_D^{20}$ –37.1° (c=1, chloroform).

EXAMPLE 28

Preparation of (−)-trans-1-Benzyl-4-(4-fluorophenyl)-3-(3,4-methylenedioxyphenoxymethyl)piperidine Hydrochloride (VIa.HCl)

To the solution of 7.54 g (0.02 mol) of (+)-cis-1-benzyl-4-(4-fluorophenyl)-3-mesyloxymethylpiperidine in 30 ml of xylene and 15 ml of sec-butanol 3 g (0.022 mol) of sesamol and the solution of 3.6 g (0.09 mol) of sodium hydroxide in 5.5 ml of water are added and the mixture is boiled under reflux for 10 hours. After taking place of the reaction 30 ml of water are added to the mixture. After separation, the organic phase is washed with water until neutral, dried over a drying agent and filtered. The filtrate is evaporated to solvent-free under reduced pressure. The evaporated residue is dissolved in 35 ml of isopropanol and acidified to pH 2 by concentrated aqueous hydrochloric acid.

The precipitated product is filtered at 0° C., washed with acetone and dried on the air to give 7.13 g (78%) of title compound, m.p.: 236–238° C.; $[\alpha]_D^{20}$ –38.0° (c=1, methanol).

EXAMPLE 29

Preparation of (−)-trans-4-(4-Fluorophenyl)-3-(3,4-methylene-dioxyphenoxymethyl)piperidine Hydrochloride Hemihydrate After suspending 8.4 g (0.02 mol) of (−)-trans-1-benzyl-4-(4-fluorophenyl)-3-(3,4-methylenedioxyphenoxymethyl)piperidine in 100 ml of distilled water in an autoclave, 2 ml of glacial acetic acid and 0.6 g of 10% palladium-on-carbon catalyst are added and hydrogenated at 30–40° C. under $2 \times 10^5$ Pa pressure. After taking up the hydrogen, the catalyst is filtered under nitrogen gas, a solution of 2 g of sodium chloride in 10 ml of water is added and the mixture is stirred at room temperature for 2 hours.

The precipitated product is filtereed at 10° C., twice washed with 5 ml of cold distilled water each and dried on air to yield 5.85 g (80%) of title compound, m.p.: 136–138° C.; $[\alpha]_D^2$ –86.50 (c=1, methanol).

The water content of the product is 2.48% (measured by Karl Fischer's method).

EXAMPLE 30

Preparation of (−)-trans-1-Benzyl-4-(4-fluorophenyl)-3-(3,4-methylenedioxyphenoxymethyl)piperidine Hydrochloride The process described in Example 28 is followed, except that 8.78 g (0.02 mol) of (+)cis-1-benzyl-4-(4-fluorophenyl)-3-bezyloxymethylpiperidine are weighed in instead of 7.54 g (0.02 mol) of (+)-cis-1-benzyl-4-(4-fluorophenyl)-3-mesyloxymethylpiperidine.

The title compound is obtained in a yield of 6.4 g (70%), m.p.: 236–238° C.; $[\alpha]_D^{20}$ –38.1° (c=1, methanol).

EXAMPLE 31

Preparation of (−)-trans-1-Benzyl-4-(4-fluorophenyl)-3-(3,4-methylenedioxyphenoxymethyl)piperidine Hydrochloride The process described in Example 28 is followed, except that 9.06 g (0.02 mol) of (+)-cis-1-benzyl-4-(4-fluorophenyl)-3-tosyloxymethylpiperidine are weighed in instead of 7.54 g (0.02 mol) of (+)-cis-1-benzyl-4-(4-fluorophenyl)-3-mesyloxymethylpiperidine.

The title compound is obtained in a yield of 6.2 g (68%), m.p.: 236–238° C.; $[\alpha]_D^{20}$ –38.0° (c=1, methanol).

EXAMPLE 32

Preparation of (−)-trans-1-Benzyl-4-(4-fluorophenyl)-3-(3,4-methylenedioxyphenoxymethyl)piperidine Hydrochloride (VIa. HCl)

To a solution containing 6.3 g (0.02 mol) of (+)-cis-1-benzyl-4-(4-fluorophenyl)-3-chloromethylpiperidine in 100 ml of isopropanol, 3 g (0.022 mol) sesamol and 3.35 g (0.03 mol) of potassium tertiary butoxide are added and the mixture is stirred at 120° C. under $4 \times 10^5$ Pa pressure for 12 hours. After taking place of the reaction, the mixture is evaporated to solvent-free and the residue is mixed with 100 ml of dichloromethane and 500 ml of water. After separation, the organic phase is washed with water until neutral and dried over a drying agent. After filtration, the filtrate is evaporated to solvent-free. The evaporation residue is dissolved in 35 ml of isopropanol and acidified to pH 2 by adding concentrated aqueous hydrochloric acid solution.

The precipitated product is filtered at 0° C., washed with acetone and dried on air to give 3.37 g (37%) of title compound, m.p.: 236–238° C.; $[\alpha]_D^{20}$ –36.9° (c=1, methanol).

What is claimed is:
1. A cis isomer of a compound having the formula

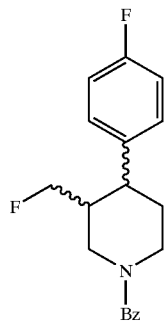

in which X is selected from the group consisting of a hydroxyl group, halogen and an R—SO$_3$— group, wherein R is unsubstituted or substituted alkyl or aryl; optically active enantiomers or racemates thereof; or a salt of these compounds.

2. A process for the preparation of paroxetine of formula (V) or salts and hydrates thereof,

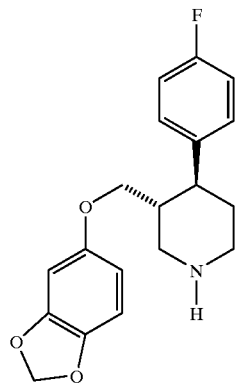

(V)

which comprises reacting a compound of formula (II)

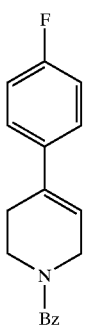

(II)

with formaldehyde in an acidic medium, to obtain a formylation product having the following formula

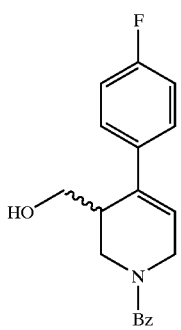

then transforming said formylation product into an acid addition salt and/or resolving said formylation product, then reducing catalytically the resulting racemic or optically active formylation product to obtain a reduction product having the following formula

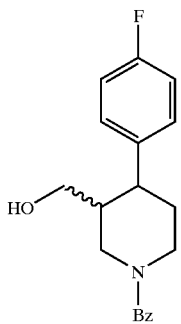

then converting said catalytic reduction product to an acid addition salt and/or resolving it, then reacting the so obtained compound with a compound of formula (III) or formula (IV)

R—SO$_2$—Y   (III)

or formula (IV)

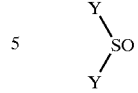

(IV)

wherein R is unsubstituted or substituted alkyl or aryl and Y is halogen to obtain a halogen or sulfonate group containing compound of the formula

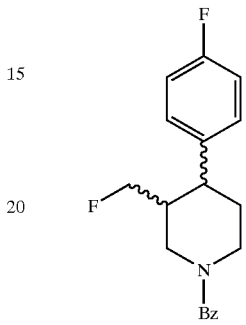

wherein X is halogen or an RSO$_3$ group wherein R is unsubstituted or substituted alkyl or aryl, then reacting said halogen or sulfonate group containing compound with sesamol to obtain a trans compound of formula (VI)

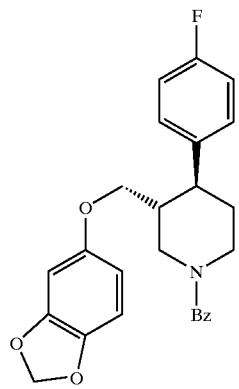

(VI)

which is either racemic or optically active, or an acid addition salt thereof, then debenzylating catalytically said compound of formula (VI) to obtain said compound of formula (V).

3. The process of claim 2, wherein said catalytic reduction product is resolved and said product compound of formula (V) is obtained as an optically active salt thereof, which is then converted to the free base.

4. The process of claim 3, wherein said free base is transformed to its hydrochloride hemihydrate.

* * * * *

UNITED STATES PATENT AND TRADEMARK OFFICE
CERTIFICATE OF CORRECTION

PATENT NO.      : 6,657,062 B1
DATED           : December 2, 2003
INVENTOR(S)     : Kreidl et al.

It is certified that error appears in the above-identified patent and that said Letters Patent is hereby corrected as shown below:

Column 16,
Line 33, "F" in the formula should be -- X --.

Column 18,
Line 20, "F" in the formula should be -- X --.

Signed and Sealed this

Eleventh Day of May, 2004

JON W. DUDAS
*Acting Director of the United States Patent and Trademark Office*